United States Patent [19]

Eggers et al.

[11] Patent Number: 5,681,282
[45] Date of Patent: Oct. 28, 1997

[54] METHODS AND APPARATUS FOR ABLATION OF LUMINAL TISSUES

[75] Inventors: Philip E. Eggers, Dublin, Ohio; Hira V. Thapliyal, Los Altos, Calif.

[73] Assignee: Arthrocare Corporation, Sunnyvale, Calif.

[21] Appl. No.: 419,886

[22] Filed: Apr. 11, 1995

Related U.S. Application Data

[63] Continuation-in-part of PCT/US94/01568, May 10, 1994, which is a continuation-in-part of Ser. No. 59,681, May 10, 1993, abandoned, which is a continuation-in-part of Ser. No. 958,977, Oct. 9, 1992, Pat. No. 5,366,443, which is a continuation-in-part of Ser. No. 817,575, Jan. 7, 1992, abandoned.

[51] Int. Cl.⁶ .................................................. A61B 17/00
[52] U.S. Cl. ............................................................ 604/114
[58] Field of Search .......................... 606/13, 14, 27, 606/28, 32, 33, 35, 37, 39, 41, 48, 50; 604/32, 114

[56] References Cited

U.S. PATENT DOCUMENTS

| | | |
|---|---|---|
| 2,050,904 | 8/1936 | Trice . |
| 4,033,351 | 7/1977 | Hetzel ........................ 606/48 |
| 4,043,342 | 8/1977 | Morrison, Jr. ............... 606/48 |
| 4,202,337 | 5/1980 | Hren et al. ................. 128/303.14 |
| 4,228,800 | 10/1980 | Degler, Jr. et al. ........ 128/303.14 |
| 4,240,441 | 12/1980 | Khalil ........................ 128/692 |
| 4,326,529 | 4/1982 | Doss .......................... 128/303.1 |
| 4,381,007 | 4/1983 | Doss .......................... 128/303.1 |
| 4,476,862 | 10/1984 | Pao ............................ 128/303.17 |
| 4,532,924 | 8/1985 | Auth et al. ................. 128/303 |
| 4,567,890 | 2/1986 | Ohta .......................... 128/303.13 |
| 4,593,691 | 6/1986 | Lindstrom et al. ......... 128/303.14 |
| 4,658,817 | 4/1987 | Hardy ........................ 128/303 |
| 4,674,499 | 6/1987 | Pao ............................ 128/303 |
| 4,709,698 | 12/1987 | Johnston et al. ........... 128/303 |
| 4,736,743 | 4/1988 | Diakuzono ................. 128/303.1 |
| 4,737,678 | 4/1988 | Hasegawa .................. 313/36 |
| 4,762,128 | 8/1988 | Rosenbluth ................ 128/343 |
| 4,765,331 | 8/1988 | Petruzzi et al. ............ 128/303 |
| 4,785,806 | 11/1988 | Deckelbaum ............... 128/303.1 |

(List continued on next page.)

FOREIGN PATENT DOCUMENTS

| | | | |
|---|---|---|---|
| 515 867 | 12/1992 | European Pat. Off. | ........ A61B 17/36 |
| 0 597 463 | 5/1994 | European Pat. Off. | ........ A61N 5/04 |
| 0 740 926 | 11/1996 | European Pat. Off. | ........ A61B 17/39 |
| WO 90/07303 WO | 7/1990 | WIPO | ........ A61B 17/39 |
| 91/136450 | 9/1991 | WIPO | ........ A61N 5/04 |
| WO 92/21278 | 12/1992 | WIPO | ........ A61B 5/04 |
| WO 93/13816 | 7/1993 | WIPO | ........ A61B 17/36 |
| WO 93/20747 | 10/1993 | WIPO | ........ A61N 1/06 |
| WO 94/04220 | 3/1994 | WIPO | ........ A61N 1/06 |
| WO 94/14383 | 7/1994 | WIPO | ........ A61B 17/36 |
| WO 94/26228 | 11/1994 | WIPO | ........ A61G 17/36 |

OTHER PUBLICATIONS

P.C. Nardella (1989) *SPIE* 1068:42–49 Radio Frequency Energy and Impedance Feedback.

Rand, J. A. et al. "Effect of Electrocautery on Fresh Human Articular Cartilage," (1985) Arthroscopy, The Journal of Arthrocopic and Related Surgery, pp. 242–246.

(List continued on next page.)

*Primary Examiner*—Manuel Mendez
*Attorney, Agent, or Firm*—Townsend and Townsend and Crew LLP

[57] ABSTRACT

An electrosurgical probe comprises a shaft having an electrode array disposed over a recessed surface at its distal end. The electrode array includes a plurality of isolated electrode terminals, and an electrosurgical power supply may be connected to the array via a connector at the distal end of the probe. The electrosurgical power supply will be provided with a plurality of independently limited or controlled current sources. By applying very high frequency electrical energy to the electric array with the power supply, target issue may be ablated while heat dissipation through low impedance past is minimized. The probe is particularly suitable for treatment of surfaces of body lumens, such as the mucosal surface within an enlarged prostate.

45 Claims, 5 Drawing Sheets

U.S. PATENT DOCUMENTS

| | | | |
|---|---|---|---|
| 4,813,429 | 3/1989 | Eshel et al. | 128/736 |
| 4,931,047 | 6/1990 | Broadwin et al. | 604/22 |
| 4,936,301 | 6/1990 | Rexroth et al. | 606/45 |
| 4,936,310 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,968,314 | 11/1990 | Michaels | 606/7 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,437 | 4/1991 | Sterzer | 428/786 |
| 5,009,656 | 4/1991 | Reimels | 606/48 |
| 5,037,421 | 8/1991 | Boutacoff et al. | 606/15 |
| 5,057,105 | 10/1991 | Malone et al. | 606/28 |
| 5,061,266 | 10/1991 | Hakky | 606/15 |
| 5,078,717 | 1/1992 | Parins et al. | 606/48 |
| 5,080,660 | 1/1992 | Buelna | 606/48 |
| 5,083,565 | 1/1992 | Parins | 128/642 |
| 5,102,410 | 4/1992 | Dressel | 606/15 |
| 5,108,391 | 4/1992 | Flachenecker et al. | 606/38 |
| 5,112,330 | 5/1992 | Nishigaki et al. | 606/46 |
| 5,125,928 | 6/1992 | Parins et al. | 606/48 |
| 5,147,354 | 9/1992 | Boutacoff et al. | 606/15 |
| 5,151,098 | 9/1992 | Loertscher | 606/16 |
| 5,178,620 | 1/1993 | Eggers et al. | 606/41 |
| 5,195,959 | 3/1993 | Smith | 604/34 |
| 5,209,273 | 3/1994 | Tan | 606/9 |
| 5,217,455 | 6/1993 | Tan | 606/9 |
| 5,249,585 | 10/1993 | Turner et al. | 607/99 |
| 5,261,410 | 11/1993 | Alfano et al. | 128/664 |
| 5,267,997 | 12/1993 | Farin et al. | 606/38 |
| 5,277,201 | 1/1994 | Stern | 607/98 |
| 5,281,216 | 1/1994 | Klicek | 606/48 |
| 5,281,218 | 1/1994 | Imran | 606/41 |
| 5,282,797 | 2/1994 | Chess | 606/9 |
| 5,290,282 | 3/1994 | Casscells | 606/29 |
| 5,300,099 | 4/1994 | Rudie | 607/101 |
| 5,301,687 | 4/1994 | Wong et al. | 607/116 |
| 5,304,170 | 4/1994 | Green | 606/9 |
| 5,312,395 | 5/1994 | Tan et al. | 606/9 |
| 5,322,507 | 6/1994 | Costello et al. | 128/4 |
| 5,326,343 | 7/1994 | Rudie et al. | 607/101 |
| 5,330,518 | 7/1994 | Neilson et al. | 607/101 |
| 5,336,217 | 8/1994 | Buys et al. | 606/9 |
| 5,366,443 | 11/1994 | Eggers et al. | 606/114 |
| 5,370,642 | 12/1994 | Keller | 606/9 |
| 5,380,316 | 1/1995 | Aita et al. | 606/7 |
| 5,383,917 | 1/1995 | Desai et al. | 607/702 |
| 5,389,096 | 2/1995 | Aita et al. | 606/15 |
| 5,419,767 | 5/1995 | Eggers et al. | 604/114 |
| 5,423,803 | 6/1995 | Tankovich | 606/9 |
| 5,445,634 | 8/1995 | Keller | 606/9 |
| 5,454,809 | 10/1995 | Janssen | 606/41 |
| 5,569,242 | 10/1996 | Lax et al. | 606/42 |

OTHER PUBLICATIONS

Buchelt, M. et al. "Excimer Laser Ablation of Fibrocartilage: An In Vitro and In Vivo Study," (1991) Lasers in Surgery and Medicine 11:271–279.

Costello, A. J. et al. "Nd:YAG Laser Ablation of the Prostate as a Treatment of Benign Prostatic Hypertrophy," (1992) Lasers in Surger and Medicine 12:121–124.

METHODS AND APPARATUS FOR ABLATION OF LUMINAL TISSUES

BACKGROUND OF THE INVENTION

The present invention is a continuation-in-part of PCT application US94/05168, filed on May 10, 1994, which was a continuation-in-part of application Ser. No. 08/059,681, filed on May 10, 1993, now abandoned, which was a continuation-in-part of application Ser. No. 07/958,977, filed on Oct. 9, 1992, now U.S. Pat. No. 5,366,443, which was a continuation-in-part of application Ser. No. 07/817,575, filed on Jan. 7, 1992, now abandoned, the full disclosures of which are incorporated herein by reference.

1. Field of the Invention

The present invention relates generally to the field of electrosurgery and, more particularly, to surgical devices and methods which employ very high frequency electrodes comprising an array of individual, isolated electrode terminals.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

The use of electrosurgical procedures in electrically conductive environments, however, can be problematic. For example, many procedures require flushing of the region to be treated with isotonic saline (also referred to as normal saline), both to maintain an isotonic environment and to keep the field of viewing clear. The presence of saline, which is a highly conductive electrolyte, can cause shorting of the electrosurgical electrode in both monopolar and bipolar modes. Such shorting causes unnecessary heating in the treatment environment and can further cause non-specific tissue destruction.

Prostate diseases, such as prostate cancer and benign prostatic hypertrophy (BPH), can cause enlargement of the prostate which in turn causes a narrowing of the urethra adjacent the prostate caused by swelling of the surrounding tissue. Such narrowing can cause difficulty in urination, resulting in discomfort and exposing the patient to further complications. A variety of methods have been proposed for treating enlarged prostates. Generally, the methods rely on either (1) reducing the prostatic mass to lessen pressure on the urethra or (2) resecting prostatic tissue adjacent the urethra in order to increase the luminal area for passing urine. The first group of methods include various protocols for directing energy, including microwave radiation, radio frequency energy, and laser energy, to induce an increase in tissue temperature within a defined volume of the prostate. Such an increase in tissue temperature, often referred to as "thermotherapy," will be maintained at a temperature and for a time sufficient to cause necrosis (death) of the treated prostate tissue, with the necrosed tissue being subsequently sloughed off or reabsorbed into the surrounding tissue mass. Such sloughing off or reabsorption of the necrosed tissue, in turn, will cause size reduction of the prostate, relieving the symptoms of BPH. The latter group of methods includes the use of endoscopes introduced through the urethra which allow for controlled tissue resection.

Of particular interest to the present invention, transurethral prostatic tissue resection techniques are known to employ monopolar "loop" electrodes introduced through conventional resectoscopes for excising tissue along the urethral lumen. The treating physician can view the procedure, either directly or over a video screen, and can control the depth of cutting by manually manipulating the position of the electrode while RF energy is applied using conventional electrosurgical power supplies.

While prostatic tissue resection using such loop electrodes is generally successful, it suffers from a number of deficiencies. First, the control of depth of cutting is difficult, placing the patient at risk of serious injury. Second, non-conductive (non-physiologic) fluids must be used to flush the region being treated in order to avoid energy dissipation through the fluid. The use of such non-physiologic irrigants, can cause trauma to the tissue and possibly disrupt the electrolyte balance in the bloodstream, resulting in hyponatremia. Third, conventional prostatic tissue resection results in the formation of tissue "chips" which must be flushed from the working site and may collect upstream in the bladder. Chip removal requires frequent withdrawal of the resectoscope in order to provide sufficient access for effective cleaning. Fourth, monopolar tissue resection can cause electrical stimulation of nearby tissue, placing the patient at risk of muscle spasms. Fifth, monopolar tissue resection can cause unintended and unwanted heating of tissue, including nerves, in regions near the intended treatment site. Such unwanted heating can result from aberrant current pathways from a treatment electrode to a dispersive electrode disposed on the patient's skin. In the worst case, unwanted heating can result in unintended tissue necrosis, leading possibly to irreversible nerve damage.

For these reasons it would be desirable to provide improved methods and apparatus for performing luminal tissue resection, particularly for performing transurethral prostatic tissue resection. Such methods and apparatus will preferably be able to overcome at least some of the problems described above in connection with conventional prostatic tissue resection. Such methods and apparatus should be able to selectively cut, ablate, and/or coagulate tissue, including the mucosal surface of the prostate, in electrically conductive environments, such as regions which are irrigated with saline, filled with blood, or the like. Such methods and apparatus should further be able to accurately control the depth of cutting and ablation of tissue, while limiting the necrosis of tissue adjacent to the treatment site. Energy levels applied by the apparatus should be precisely controlled and should be sufficient to provide energy densities adequate for rapid cutting and ablation. Use of the devices should not be limited to prostatic tissue resection, and should be adaptable to the treatment of a wide variety of luminal surfaces.

2. Description of the Background Art

Resectoscopes and other devices employing radio frequency and other energy for the hyperthermic treatment of prostatic tissue are described in U.S. Pat. Nos. 5,330,518; 5,326,343; 5,322,507; 5,301,687; 5,300,099; 5,249,585; 5,112,330; 5,061,266; 5,112,330; 5,061,266; 5,007,437; 4,967,765; 4,813,429, and 4,762,128; PCT Applications WO 91/13650 and 94/04220; and European Application 597 463. See also Costello et al. (1992) *Lasers in Surgery and Medicine* 12:121–124.

Parent Application PCT US 94/05168 has been published as WO 94/26228, and great great grandparent Application U.S. Ser. No. 07/958,977, has issued as U.S. Pat. No. 5,366,443. The '443 patent suggests that the disclosed catheters are useful for treating enlarged prostates.

Devices incorporating radio frequency electrodes for use in electrosurgical and electrocautery techniques are described in Rand et al. (1985) *J. Arthro. Surg.* 1:242–246 and U.S. Pat. Nos. 5,281,216; 4,943,290; 4,936,301; 4,593,691; 4,228,800; and 4,202,337. U.S. Pat. No. 5,281,216 describes a bipolar device having an active electrode coated with a high impedance material where the differential impedance between the active and return electrodes is optimized to provide a desired cutting effect. Vascular catheters and devices incorporating radio frequency electrodes to assist in penetrating atheroma and plaque are described in U.S. Pat. Nos. 5,281,218; 5,125,928; 5,078,717; 4,998,933; and 4,976,711, and PCT publications WO 93/20747 and WO 90/07303, the latter of which describes a catheter having four isolated electrode surfaces at its distal end. Electrosurgical power supplies including power controls and/or current limiting systems are described in U.S. Pat. No. 5,267,997 and PCT publication WO 93/20747. Surgical lasers for cutting and ablation in arthroscopic and other procedures are described in Buchelt et al. (1991) Surgery and Medicine II:271–279; and U.S. Pat. Nos. 5,147,354; 5,151,098; 5,037,421; 4,968,314; 4,785,806; 4,737,678; 4,736,743; and 4,240,441.

SUMMARY OF THE INVENTION

The present invention provides methods and apparatus for selectively applying electrical energy against the wall of a body lumen to ablate luminal tissue and enlarge the available luminal area. The methods and apparatus are particularly useful for treating prostatic diseases, such as prostate cancer and benign prostatic hypertrophy (BPH), which conditions can result in partial or total occlusion of the urethra.

Methods according to the present invention comprise engaging an electrode array including a plurality of electrically isolated electrode terminals against a wall of the body lumen, such as against the mucosal surface of the prostate within the urethra. The electrode array will usually be present at the distal end of a probe, wherein the probe may be introduced by conventional transurethral or suprapubic access roots. In the case of transurethral introduction, the probe will typically be passed through a conventional viewing scope having a working lumen, such as a resectoscope. After positioning the electrode array at the target site, high frequency voltage is applied between the array and one or more common electrodes, in either a monopolar or a bipolar manner. A laterally outward force is applied on the electrode array to ablate peripheral tissue in the lumen, typically in combination with axial and/or transverse translation of the surface to effect the desired depth of ablation.

Apparatus according to the present invention include an electrosurgical probe comprising a shaft having a proximal end, a distal end, and a recessed surface near the distal end. An electrode array is disposed over at least a portion of the recessed surface and includes a plurality of electrically isolated electrode terminals. A connector is provided near the proximal end of the shaft for electrically coupling the electrode terminals of the array to a high frequency voltage source. The recessed surface may be planar, convex, or a combination thereof, and is usually formed over a transverse, coaxial plane which is spaced radially inward from a cylindrical surface of the shaft. The shaft may be flexible or rigid, usually being rigid over at least a distal portion thereof to facilitate the application of lateral force during use. A common electrode is optionally provided on the shaft. Alternatively, one or more common electrode(s) may be disposed within the electrode array itself to provide for bipolar operation. In a preferred aspect, each electrode terminal will be connected to the proximal connector by an electrically isolated conductor disposed within the shaft. In that way, the electrode terminals may be connected to a high frequency power supply, with energy distribution to the terminals controlled entirely by the power supply.

The methods and apparatus of the present invention are advantageous in numerous aspects, particularly with respect to the ablation of prostatic tissue. The ability to control current flow through individual electrode terminals minimizes power dissipation into the surrounding medium. Such limited power dissipation, in turn, permits the use of electrolytic irrigants, such as isotonic saline, which has a number of physiologic advantages. Moreover, ablation over the relatively large area afforded by the electrode array surface minimizes the generation of larger particles of tissue, which in turn minimizes the need to withdraw the probe (and in some cases associated resectoscope) in order to flush the area being treated. Use of the electrode array also allows for careful control of the depth of ablation, particularly when used with an associated resectoscope or other direct viewing apparatus. The ability to operate in a bipolar mode also reduces the risk of unwanted electrical stimulation which can cause muscle spasms and can limit the depth of tissue necrosis during ablative resection.

A further understanding of the nature and advantages of the invention will become apparent by reference to the remaining portions of the specification and drawings.

DESCRIPTION OF THE SPECIFIC EMBODIMENTS

The present invention provides methods and apparatus for selectively ablating tissue within a patient's body lumen, particularly including peripheral luminal tissues, such as prostatic mucosal tissues located within the male urethra. Due to enlargement of the prostate gland, the urethral passage in the male can be totally or partially occluded. By ablating the mucosal surface of the prostate gland where the occlusion occurs, the urethra can be opened to alleviate symptoms of the disease, such as difficulty in urination. The methods and apparatus of the present invention, however, are not meant to be limited to the treatment of prostatic tissues, but rather can be employed in the treatment of any luminal surface within a patient body lumen, including hollow body organs where treatment of a mucosal or endothelial surface may be desired.

The present invention utilizes an electrode array including a plurality of independently current-limited and/or power controlled electrode terminals distributed over a recessed contact surface near the distal end of the probe. By laterally engaging the electrode array against the target tissue, energy can be applied in electrically conductive environments, such as saline, blood, or the like, while limiting unwanted heating of saline, blood, and other conductive substances, in the surrounding environment. Use of the recessed electrode array surface is particularly advantageous when the probe is to be introduced through a working lumen of a resectoscope or other access device.

The electrosurgical probe will comprise a shaft having a proximal end and a distal end, with the recessed surface near the distal end. The shaft may be flexible, rigid, or a combination thereof. For example, when the probe is to be introduced through the working channel of a resectoscope, it will be desirable that at least the proximal end of the shaft have sufficient rigidity so that the electrode array can be laterally deflected with sufficient force to achieve the desired ablation. When the shaft is introduced transurethraly over a guidewire, or suprapubically through an incision, the shaft may be either rigid or flexible. Flexible shafts may be laterally deflected using an internal stylet (which can be temporarily placed to increase rigidity), internal deflecting means such as pullwires, or the like. A wide variety of particular probe configurations can be devised for treatment of prostatic tissues according to the methods of the present invention.

The electrode array will have a total surface (i.e. tissue contact) area in the range from 1 $mm^2$ to 75 $mm^2$, preferably from 2 $mm^2$ to 40 $mm^2$, and will usually include at least two isolated electrode terminals, more usually at least four electrode terminals, preferably at least six electrode terminals, more preferably at least eight electrode terminals, even more preferably at least 15 electrode terminals, and still more preferably at least 20 electrode terminals, and sometimes 50 or more electrode terminals, usually being in the range from 2 to 50 individual electrode terminals, disposed over the distal contact surfaces on the shaft. By contacting the electrode array(s) on the contact surface(s) against target tissue and applying high frequency voltage between the array(s) and an additional common or return electrode in direct or indirect contact with the patient's body, the target tissue is selectively ablated, permitting selective removal of portions of the target tissue while desirably minimizing the depth of necrosis to surrounding tissue. In particular, this invention provides a method and apparatus for effectively ablating and cutting adenomatous tissue within the prostate or tumor-tissue within the prostate or bladder by simultaneously applying (1) electrical energy to the target tissue surrounding and immediately adjacent to the tip of the probe and (2) lateral pressure against the target tissue using the probe itself, and (3) optionally moving the electrode array axially and/or transversely over the tissue.

Each individual electrode terminal in the electrode array is electrically insulated from all other electrode terminals in the array within said probe and is connected to a power source which is isolated from each of the other electrodes in the array or to circuitry which limits or interrupts current flow to the electrode when low impedance material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuable switches or may be provided by independent current limiting elements, such as inductors, capacitors, resistors, and/or combinations thereof.

The tip region of the probe is thus composed of many independent electrode terminals designed to deliver electrical energy in the vicinity of the tip. The selective heating of the target tissue is achieved by connecting each individual electrode terminal and the common electrode (e.g., a band of conductive material proximal to the electrode array at the tip or an external electrode which is placed on the outside of the patient's body) to a power source having independently controlled or current-limited channels. The application of high frequency voltage between the common electrodes and the electrode array results in the conduction of high frequency current from each individual electrode terminal to the said common electrode. The current flow from each individual electrode terminal to the common electrodes is controlled by either active or passive means, or a combination thereof, to deliver electrical energy to the target tissue while minimizing energy delivery to surrounding (non-target) tissue and any conductive fluids which may be present (e.g., blood, electrolytic irrigants such as saline, and the like).

In a preferred aspect, this invention takes advantage of the differences in electrical properties between the target tissue (e.g., prostatic or other peripheral luminal tissue) and the surrounding conductive liquid (e.g., isotonic saline irrigant) in the region immediately adjacent to the electrode array since the majority of impedance occurs in the space within several millimeters of each electrode terminal. By way of example, for any selected level of applied voltage, if the electrical conduction path between the common electrode and one of the individual electrode terminals within the electrode array is isotonic saline irrigant liquid (having a relatively low electrical impedance), said current control means connected to the individual electrode will limit current flow so that the heating of intervening conductive liquid is minimized. In contrast, if a portion of or all of the electrical conduction path between the common electrode and one of the individual electrode terminals within the electrode array is prostatic tissue (having a relatively higher electrical impedance), said current control circuitry or switch connected to said individual electrode will allow current flow sufficient for the heating or ablation or electrical breakdown of the target tissue in the immediate vicinity of the electrode terminal surface.

The application of a high frequency voltage between the common or return electrode and the electrode array for appropriate time intervals effects ablation (volumetric removal), the target tissue. The tissue volume over which energy is dissipated (i.e., a high voltage gradient exists) may be precisely controlled, for example, by the use of a multiplicity of small electrodes whose effective diameters range from about 0.01 mm to 2 mm, preferably from about 0.05 mm to 1 mm, and more preferably from about 0.1 mm to 0.5 mm. Electrode terminal areas for both circular and non-circular terminals will have a contact area (per electrode) below 5 mm², preferably being in the range from 0.0001 mm² to 1 mm², and more preferably from 0.005 mm² to 0.5 mm². The use of small diameter electrode terminals reduces the extent and depth of tissue necrosis as a consequence of the divergence of current flux lines which emanate from the exposed surface of each electrode terminal. Energy deposition in tissue sufficient for irreversible damage (i.e., necrosis) has been found to be limited to a distance of about one-half to one electrode terminal diameter. This is a particular advantage over prior electrosurgical probes employing single and/or larger electrodes where the depth of tissue necrosis may not be sufficiently limited. Heretofore, increased power application and ablation rates would usually be achieved by increasing the electrode area. Surprisingly, with the present invention, it has been found that the total electrode area can be increased (to increase power delivery and ablation rate) without increasing depth of necrosis by providing multiple small electrode terminals. Preferably, the terminals will be spaced-apart by a distance in the range from one-half diameter to one diameter for optimum power delivery, as discussed below. The depth of necrosis may be further controlled by switching the applied voltage off and on to produce pulses of current, said pulses being of sufficient duration and associated energy density to effect ablation and/or cutting while being turned off for periods sufficiently long to allow for thermal relaxation between energy pulses. In this manner, the energy pulse duration, magnitude and the time interval between energy pulses are selected to achieve efficient rates of tissue ablation or cutting while allowing the temperature of the heated zone of tissue to "relax" or approach to normal physiologic temperatures (usually to within 20° C. of normal temperature (37° C.), preferably to within 10° C.) before the onset of the next energy (current) pulse.

The rate of energy delivery to the target tissue is controlled by the applied voltage level and duty cycle of the voltage pulse. The use of high frequency current minimizes induced stimulation of muscle tissue or nerve tissue in the vicinity of the body structure being treated. In addition, high frequencies minimize the risk of interfering with the natural pacing of the heart in circumstances where the probe of the present invention is used near the heart.

The power applied to the common electrode and the electrode array will be at high or radio frequency, typically between about 20 kHz and 20 MHz, usually being between about 30 kHz and 1 MHz, and preferably being between about 50 kHz and 400 kHz. The RMS (root mean square) voltage applied will usually be in the range from about 5 volts to 1000 volts, preferably being in the range from about 50 volts to 800 volts, and more preferably being in the range from about 10 volts to 500 volts. Usually, the current level will be selectively limited or controlled and the voltage applied will be independently adjustable, frequently in response to the resistance of tissues and/or fluids in the pathway between an individual electrode and the common electrode. Also, the applied current level may be in response to a temperature control means which maintains the target tissue temperature within desired limits at the interface between the electrode arrays and the target tissue. The desired temperature of the target tissue along a propagating surface just beyond the region of necrosis will usually be in the range from about 40° C. to 500° C., and more usually from about 50° C. to 300° C. The necrosed tissue immediately adjacent the electrode array may reach even higher temperatures.

The preferred power source of the present invention delivers a high frequency current selectable to generate average power levels ranging from tens of milliwatts to tens of watts per electrode, depending on the target tissue being heated, the rate of ablation desired or the maximum allowed temperature selected for the probe tip. The power source allows the user to select the current level according to the specific requirements of a particular urological procedure involving either endoscopic or open surgical access to the target site.

The power source will be current limited or otherwise controlled so that undesired heating of electrically conductive fluids or other low electrical resistance tissues does not occur. In a presently preferred embodiment of the present invention, current limiting inductors are placed in series with each independent electrode terminal, where the inductance of the inductor is in the range from 50 µH to 5000 µH. Alternatively, capacitor-inductor (LC) circuit structures may be employed, as described in more detail below. Additionally, a current limiting resistor may be selected having a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant). Thus, the electrode terminal sees a relatively constant current source so that power dissipation through a low resistance path, e.g., normal saline irrigant, will be substantially diminished.

As an alternative to such passive circuit structures, constant current flow to each electrode terminal may be provided by a multi-channel power supply. A substantially constant current level for each individual electrode terminal within a range which will limit power delivery through a low resistance path, e.g., isotonic saline irrigant, would be selected by the user to achieve the desired rate of ablation. Such a multi-channel power supply thus provides a constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

The electrode array is formed over a contact surface near the distal end of the shaft of the electrosurgical probe. Preferably, the contact surface will be recessed relative to at least a portion of the shaft proximal to the contact surface. In the exemplary embodiment, the shaft will be cylindrical over most of its length, with the contact surface being formed as a coaxial, transverse (usually planar or slightly convex) section at the distal end of the shaft. Such a recessed contact surface is advantageous since it helps protect and shield the electrode terminals on the surface while they are being introduced, particularly while being introduced through the working channel of the resectoscope or other viewing scope.

The area of the contact surface can vary widely, with areas typically being in the range from 1 $mm^2$ to 75 $mm^2$, usually being from 2 $mm^2$ to 40 $mm^2$. The electrode contact surface will usually be planar or slightly concave in order to enhance contact with peripheral luminal tissue when the probe is laterally engaged against the tissue. Optionally, electrode terminals may also be formed over a forwardly disposed surface of the probe, such as over the distal tip of the probe, to enhance penetration of the probe through fully occluded body lumens, where the probe must be advanced axially through the occluding tissue.

The contact surfaces of the electrode terminals may be raised above the contact surface of the probe by a preselected distance, typically by up to about 2 mm, usually up to about 1 mm. It has been found that electrode terminals which protrude by a greater distance above the underlying contact surface achieved more rapid surface ablation of tissue. Electrode terminals having contact surfaces which protrude less, achieve more controlled tissue ablation and maximize hemostasis. Thus, in certain procedures, it may be desirable to first remove tissue using a probe having contact surfaces which extend by a distance selected within the range from 0.25 mm to 0.8 mm above the underlying contact surface, followed by treatment with a probe having terminals with contact surfaces which extend by a lesser distance, typically selected within the range from 0 mm to 0.2 mm above the underlying contact surface to shape and contour the tissue surface.

Referring now to FIGS. 1-4, an exemplary electrosurgical system 10 comprises an electrosurgical probe 12, a power supply 14, and a connecting cable 16. Probe 12 includes a connector 18 at its proximal end and an electrode array 20 at its distal end. Connecting cable 16 includes a connector 22 at its distal end and is permanently or removably attached to the power supply 14 at its proximal end 24. Connector 18 on the electrosurgical probe 12 removably connects to the connector 22 on the cable 16. Each connector includes a plurality of isolated individual conductors for electrically coupling individual electrode terminals 28 in the array 20 to the power supply 14, as will be described in more detail below.

The electrode array 20 comprises a plurality of electrically isolated electrode terminals 28 which are spaced-apart over an electrode array surface 30. The electrode array surface 30 and the individual electrode terminals 28 will usually have dimensions within the ranges set forth above. In the exemplary embodiment, the electrode surface has a length L (FIG. 3) in the range from 1 mm to 20 mm and a width W in the range from 0.5 mm to 7 mm. The individual electrode terminals 28 will protrude over the electrode array surface 30 by a distance H (FIG. 4) from 0 to 2 mm, preferably from 0 mm to 1 mm. As described above, electrode terminals which are flush with the surface, or protrude by a minimum distance, usually below about 0.2 mm, will provide less aggressive ablation and are particularly suitable for smoothing of treated tissue surfaces and providing hemostasis to inhibit or prevent bleeding of treated surfaces. Conversely electrodes which protrude more than about 0.25 mm will provide more aggressive tissue ablation.

Figure 1:
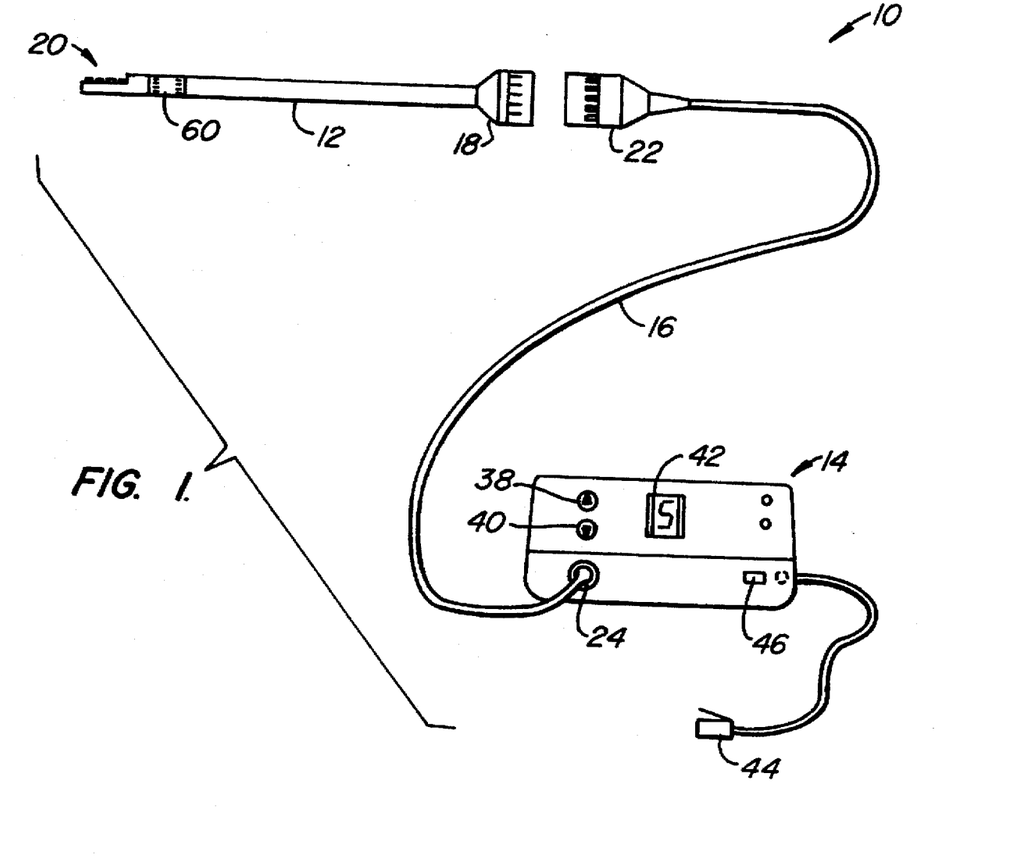
FIG. 1 is a perspective view of an electrosurgical system including an electrosurgical probe and electrosurgical power supply constructed in accordance with the principles of the present invention.
Figure 2:
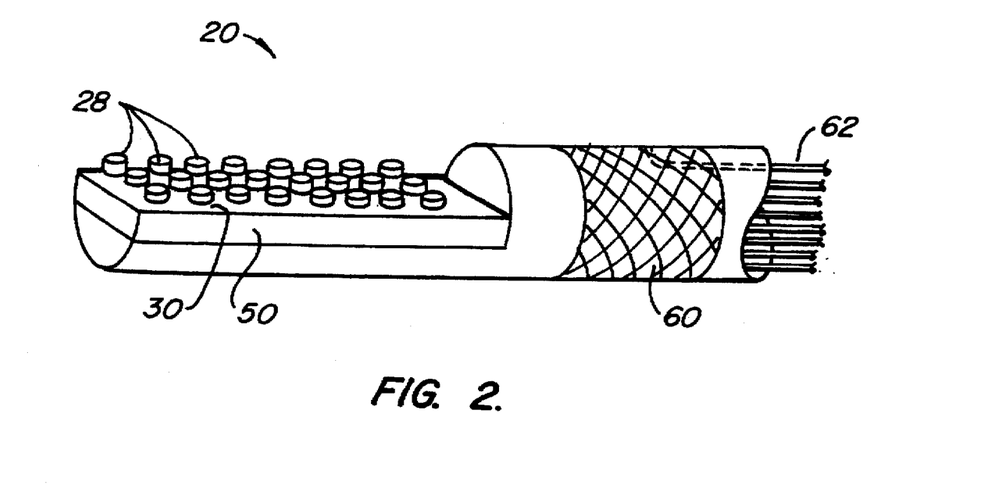
FIG. 2 is an enlarged, detailed view of the distal tip of the electrosurgical probe of FIG. 1.

The power supply 14 will usually include power level control means, such as power increase button 38 and decrease button 40, a power level indicator display 42, a foot pedal 44 which allows the treating physician to selectively energize the power supply non-manually, a power switch 46, and optionally other controls. The specific design of an exemplary power supply which may be used with the electrosurgical system and electrosurgical probe of the present invention is described in parent application PCT US 94/05168, the full disclosure of which has previously been incorporated herein by reference.

The individual electrode terminals 28 which comprise the electrode array 20 at the distal end of electrosurgical probe 12 are preferably arranged in a closely-spaced pattern and are anchored within an electrically insulating support matrix 50. The electrically insulating support matrix 50 is in turn adhesively joined to an electrically insulating potting material 51, such as an epoxy or silicone-based material. In a preferred construction technique, the electrode terminals 28 extend through pre-formed openings in the support matrix 50 so that they protrude above the surface 30 by the desired distance H. The electrodes are then bonded to the back face 52 of the support matrix 50, typically by an inorganic sealing material 31. The electrode terminals 58 are composed of a refractory, electrically conductive metal or alloy, such as platinum, platinum alloys, titanium, titanium alloys, and the like. The support matrix 50 is typically formed from a ceramic or glass material, such as alumina, zirconia, and the like. Platinum is the preferred choice for electrode terminal material since it is bio-compatible, has a low erosion rate, and is readily fabricated and attached to leads 54 within the shaft of the electrosurgical probe 12, as described in more detail with reference to FIG. 5 below. The preferred support matrix material is yttria-stabilized zirconia, such as zirconia Z-201N available from Kyocera Industrial Ceramics Corporation, Elkgrove, Ill., because of its high flexural modules, bio-compatibility, and high melting point. The inorganic sealing material 31 is selected to provide good electrical insulation, good adhesion to the zirconia, and good adhesion to the platinum electrode terminals, with a compatible thermal expansion coefficient and melting point well below that of the platinum and the zirconia, typically being a glass or ceramic.

In the exemplary embodiment, a return electrode 60 is located on the exterior of the shaft of electrosurgical probe 12, typically being spaced from 1 mm to 10 mm proximally of the proximal end of the electrode array surface 30 and having a length in the range from 2 mm to 10 mm. The return electrode 60 may fully or partially circumscribe the exterior surface of the cylindrical probe body, and may optionally comprise a coiled, flat-wire cannula formed over the exterior surface of the proximal portion of the probe. The electrically conductive coiled cannula will be covered with a flexible, electrically insulating layer over most of its proximal portion, leaving only the distal end exposed to provide the desired exposure to the isotonic saline irrigant to provide for the return current path. Alternatively, the return electrode 60 may comprise a simple band electrode having an elongate conductor 62 (FIG. 2) providing for connection at the proximal connector 18.

Figure 5:
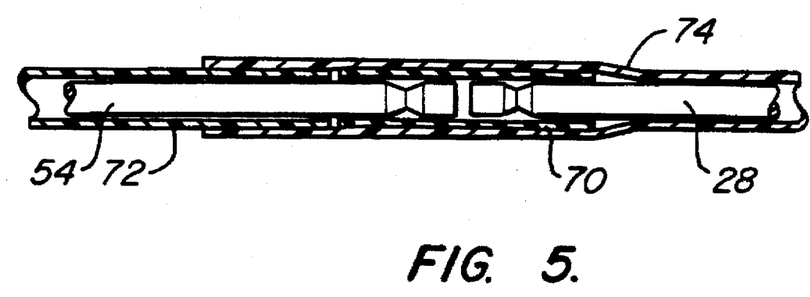
FIG. 5 is a detailed view of a connection assembly for the electrodes of the electrosurgical probe of FIGS. 1 and 2.

Referring now to FIG. 5, it is desirable to connect the proximal end of an electrode terminal 28 composed of a precious metal, such as platinum, to an electrical lead 54, composed of copper or other low value conductor material. A preferred method for forming the connection comprises placing a tin or gold-plated ferrule 70 over adjoining ends of the terminal 28 and lead 54. The copper electrical lead 54 is covered with a layer of insulation 72 up to the ferrule 70. A second layer of insulation 74 extends over the electrode terminal 28, the ferrule 70, and overlaps with the first layer of insulation 72. Preferably, the ferrule will be crimped over each end of the electrode terminal 28 and lead 54, respectively, as illustrated.

Figure 3:
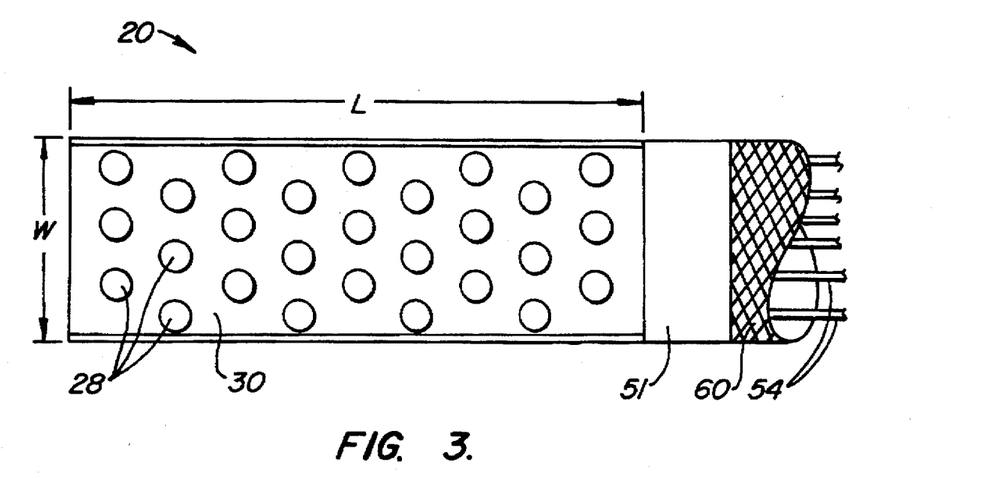
FIG. 3 is a plan view of the distal tip of the electrosurgical probe of FIGS. 1 and 2.
Figure 4:
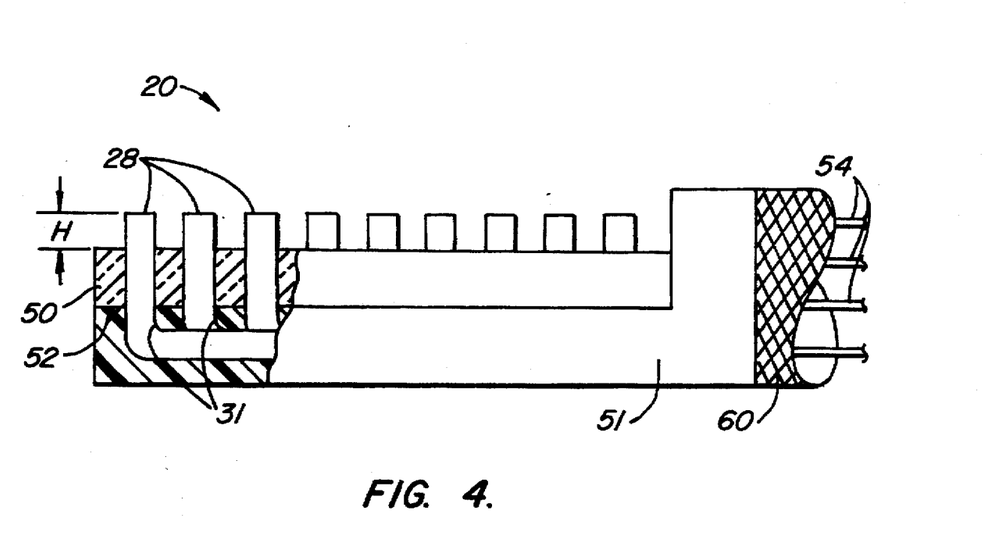
FIG. 4 is an elevational view of the distal tip of the electrosurgical probe of FIGS. 1 and 2.
Figure 5A:
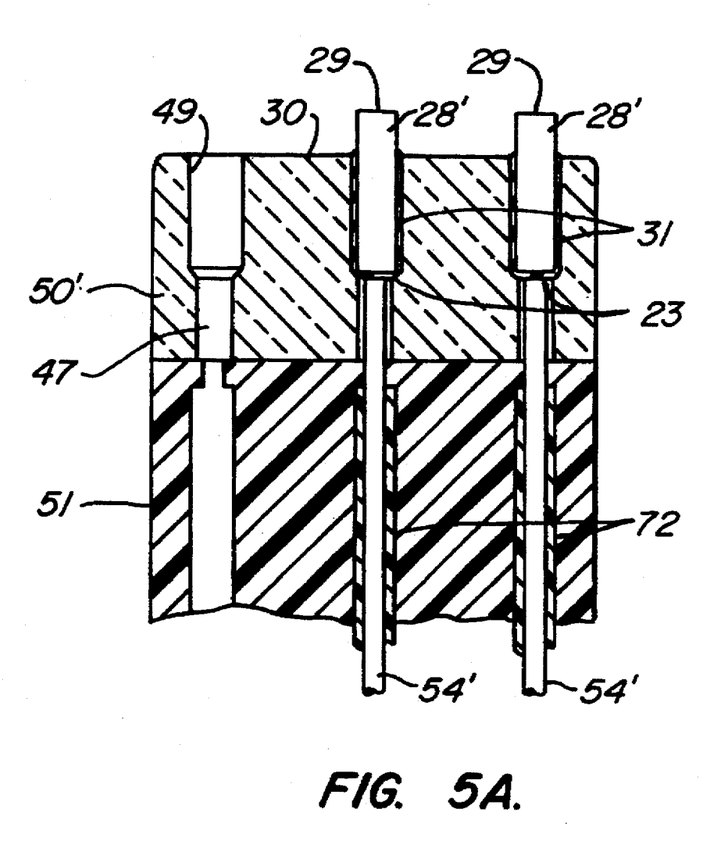
FIG. 5A is an alternative construction of a distal tip of a probe similar to that shown in FIG. 4.

An alternative structure for connecting electrode terminals 28 to conductors 54 in the electrode array 20 of probe 12 in FIG. 3, is shown in FIG. 5A. FIG. 5A is an alternative transverse cross-section of the array 20 of FIG. 4. For convenience, conductors 54' in FIG. 5A are shown in a downward direction only. In an actual device, conductors 54' would be turned in a proximal direction (i.e. into the page as shown in FIG. 5A) to proceed axially down the probe.

An electrically insulating support matrix 50' is formed with an array of holes having a large diameter upper portion 49 and a reduced diameter lower portion 47. The large diameter upper portion 49 is sized to loosely accommodate electrode terminal 28', where the depth of portion 49 determines the distance with which the contact area 29 of each electrode terminal 28' is disposed over the front face 30 of the support matrix 50'. The small diameter portion 47 is too small to permit entry of the electrode terminal 28', but is sufficiently large to receive the conductor 54' therethrough. For convenience, the electrode terminal 28' and conductor 54' are not shown in the left-most electrode cavities of the cross-section of FIG. 5A.

The design of FIG. 5A is particularly advantageous with electrode terminals 28' formed from precious metals, such as platinum. By limiting the depth of the upper portion 49 to a relatively small distance, typically from 0.2 mm to 3 mm, preferably from 0.5 mm to 1.5 mm, the amount of material in each electrode is greatly reduced. By then forming the conductor 54' from a less precious metal, such as copper, the cost of the probe 12 can be lessened.

The embodiment illustrated in FIG. 5A can be fabricated by first forming the array of holes in the electrically insulating support matrix 50. The matrix 50 will typically be composed of one of the materials set forth above, such as alumina or zirconia. The electrode terminals 28' are then placed in the holes and bonded to the support matrix 50' at its front face 30, typically using an inorganic sealing material 31, such as a glass or glass/ceramic material. The electrical conductors 54' are next engaged against the lower surfaces of the electrode terminals 28' by passing them through the smaller diameter portions 47. An electrically conductive Joint 33 is next formed, typically using solder, braising, welding, or an electrically conductive adhesive, such as silver-filled epoxy, available from manufacturers such as TRA-CON, Inc. Medford, Mass. The remaining lengths of the conductor 54' can then be formed as desired, and the conductors embedded in a potting material 51, optionally being encased in a layer of insulation 72.

The electrosurgical probe 12 may be introduced to a treatment site using any known minimally invasive or open surgical introducing technique. In the preferred case of prostate treatment, the probe may be introduced through the patient's urethra (transurethrally) or via a suprapubic incision. In the case of transurethral introduction, the probe may be introduced over a guidewire (probe can be readily modified to include a central guidewire lumen), or preferably will be introduced through a resectoscope, as will now be described.

Figure 6:
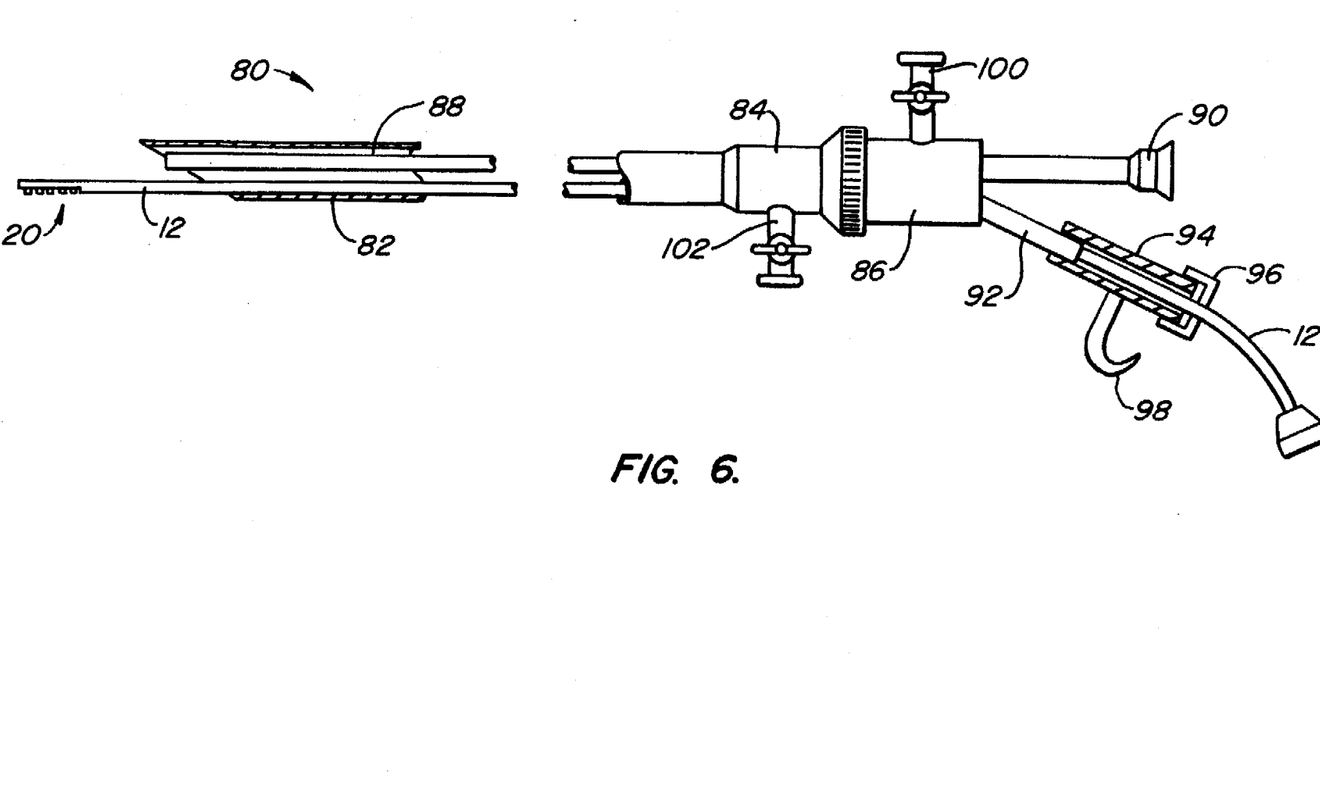
FIG. 6 is an assembly drawing showing the electrosurgical probe of FIGS. 1 and 2 present in the working lumen of a resectoscope.

Referring now to FIG. 6, probe 12 can be inserted through a resectoscope 80 comprising a tubular shaft 82, a proximal housing 84, and a coupling housing 86. The resectoscope may be of conventional construction, including a telescope lumen 88 having a terminal coupling 90 at its proximal end. The probe 12 may be introduced through the lumen of the shaft 82, typically through a proximal connection leg 92. In the preferred embodiment, the proximal end of probe 12 will be locked in an axially translatable holder 94 which is sealingly received over the connector leg 92. The probe 12 is locked in place, and a finger or thumb loop 98 allows the treating physician to extend and retract electrode array 20 relative to the distal end of the resectoscope. As a particular advantage, use of the resectoscope permits viewing of the region being treated with the electrode array 20 through the telescope 88. The viewing field will be kept clear with irrigant, typically isotonic saline, introduced through a connector 100 which passes the fluid through the telescope lumen 88. Fluid will be withdrawn through a second connector 102 which can be connected to a suitable vacuum source to withdraw contaminated fluid from the region being treated. As a particular advantage, the debris generated by the electrosurgical ablation of the present invention will generally be very fine, allowing it to be withdrawn through the connector by conventional vacuum aspiration techniques.

Referring again to FIG. 1, the length of the electrosurgical probe 12 can be in the range from 5 cm to 100 cm, depending on the location of the lumen being treated and the method of access used. Often devices intended for endoscopic insertion will be longer than those used in open surgical procedures. The diameter of the electrosurgical probe 12 can be in the range from 0.5 mm to about 5 mm, again depending on the lumen being treated and manner of introducing the probe.

Figure 7:
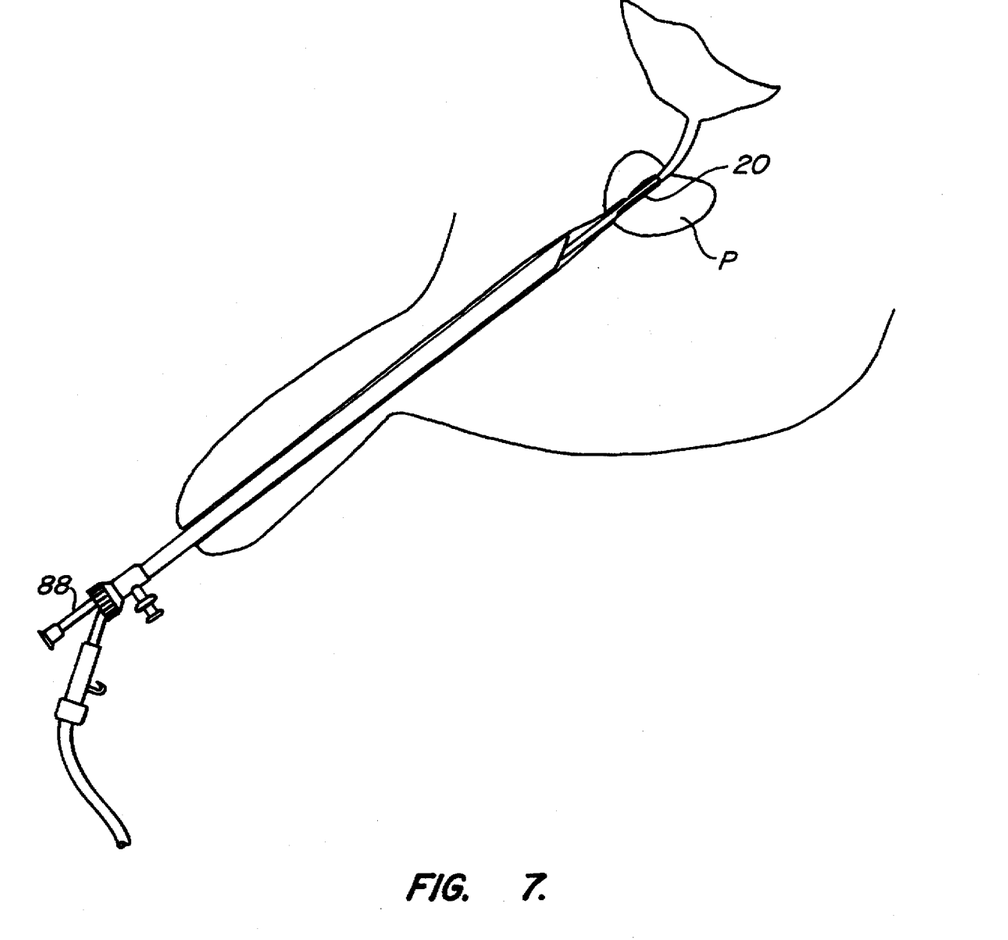
FIG. 7 illustrates use of the probe-resectoscope assembly of FIG. 6 in treatment of an enlarged prostate.

Referring now to FIG. 7, use of the resectoscope assembly of FIG. 6 for treating an enlarged prostate P will be described. The electrode surface 20 is introduced transurethrally to the urethra within the prostate P, as illustrated. While viewing the region via telescope 88, power can be applied to the electrode array 20 from the power supply 14 (FIG. 1). As described previously, power will be selectively applied to the tissue which is in contact with individual electrode terminals. Such selective energy transfer provides rapid, controlled ablation without the undesirable side effects discussed above. Ablation is achieved by laterally engaging the electrode surface against the mucosal surface of the prostatic tissue, typically while moving the electrode array axially, transversely, or a combination of the two motions. The tissue ablation will continue until the luminal cross-sectional area has been increased by a desired amount. The resectoscope can then be withdrawn from the urethra. Optionally, rapid tissue ablation can initially be achieved using a probe 12 having electrode terminals 28 which extend over the electrode surface by a relatively larger distance. After the desired amount of tissue has been removed, the surface can be smoothed using a second electrosurgical probe having individual electrode terminals which extend over the underlying surface by a lesser distance. Such smoothing will usually also result in sealing transected blood vessels to provide hemostasis.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for enlarging a body lumen within a patient body, said method comprising:
   engaging an electrode array including a plurality of electrically isolated electrode terminals against a wall of the body lumen;
   applying high frequency voltage between each electrode terminal in the electrode array and on or in the patient body; and
   applying laterally outward force on the electrode array while applying the high frequency voltage to ablate peripheral tissue in the lumen.

2. A method as in claim 1, wherein the body lumen is the urethra and the electrode array is engaged against the mucosal surface of the prostate.

3. A method as in claim 2, further comprising introducing the electrode array transurethrally prior to engaging the electrode array against the mucosal surface of the prostate.

4. A method as in claim 3, further comprising introducing the electrode array suprapubically prior to engaging the electrode array against the mucosal surface of the prostate.

5. A method as in claim 1, further comprising introducing a viewing scope having a working lumen to the body lumen and viewing a target location in the body lumen and viewing a target location in the body lumen,
   wherein the electrode array is introduced through the working lumen prior to engaging against the body lumen wall.

6. A method as in claim 1, wherein current flow from at least two of said electrode terminals is independently controlled based on impedance between the electrode terminal and the common electrode.

7. A method as in claim 6, wherein current flow is limited when a low impedance path exists between the electrode terminal and the common electrode.

8. A method as in claim 6, wherein current flow is limited when a high impedance path exists between the electrode terminal and the common electrode.

9. A method as in claim 1, wherein the high frequency voltage is in the range from 20 kHz to 20 MHz and in the range from 5 volts to 300 volts (RMS).

10. A method as in claim 1, further comprising measuring temperature at an interface between the electrode array and the lumen wall and controlling the voltage, current, or duty cycle to maintain a preset interface temperature.

11. A method as in claim 1, wherein the electrode array is present in an electrically conductive environment.

12. A method as in claim 11, wherein the electrically conductive environment comprises saline.

13. A method as in claim 1, wherein the electrode array is disposed at the distal end of a cylindrical shaft and is recessed relative to a proximal portion of the shaft.

14. A method as in claim 13, wherein the electrode array has an area in the range from 1 $mm^2$ to 75 $mm^2$.

15. A method as in claim 14, wherein the electrode array consists of from 2 to 50 individual electrode terminals.

16. A method as in claim 15, wherein the individual electrode terminals each have contact surfaces with a cross-sectional area in the range from 0.0001 $m^2$ to 1 $mm^2$.

17. A method as in claim 16, wherein the individual electrode terminals protrude over the recessed surface by a distance in the range from 0 mm to 2 mm.

18. The method of claim 1 wherein high frequency voltage is applied between at least three electrode terminals in the electrode array to one or more common electrodes.

19. The method of claim 1 wherein high frequency voltage is applied between at least five electrode terminals in the electrode array to one or more common electrodes.

20. The method of claim 1 wherein high frequency voltage is applied between each of at least two electrode terminals and a single common electrode disposed proximally from the electrode terminals.

21. A method as in claim 1 wherein the electrode terminals have an inherent capacitance, the method further comprising delivering high frequency current across at least one current limiting element in series with one of the electrode terminals.

22. A method as in claim 21 further comprising selecting the current limiting element such that the capacitance of each electrode terminal and the associated current limiting element together form a series resonant output circuit.

23. A method as in claim 21 wherein the current limiting element comprises an inductor.

24. A method as in claim 23 further comprising positioning at least on capacitor in series with each inductor to form a lumped capacitance.

25. An improved method for treating prostate disease of the type wherein energy is applied to the mucosal surface of the prostate, wherein the improvement comprises engaging an electrode array against the mucosal surface and applying high frequency voltage to the electrode array under conditions where current flow from individual terminals from the electrode array is limited to inhibit power loss through low impedance paths from the electrode array.

26. An electrosurgical probe comprising:
   a shaft having a proximal end, a distal end, and a recessed surface near the distal end;
   an electrode array disposed over the recessed surface near the distal end of the shaft, said array including a plurality of electrically isolated electrode terminals having substantially the same potential; and
   a connector disposed near the proximal end of the shaft for electrically coupling the electrode terminals to a high frequency voltage source.

27. An electrosurgical probe as in claim 26, wherein the shaft has a length in the range from 5 cm to 50 cm and an outer diameter in the range from 0.5 mm to 5 mm.

28. An electrosurgical probe as in claim 27, wherein the shaft is flexible along at least a portion of its length.

29. An electrosurgical probe as in claim 28, wherein at least a distal portion of the shaft is rigid.

30. An electrosurgical probe as in claim 27, wherein the electrode array consists of from 2 to 50 individual electrode terminals.

31. An electrosurgical probe as in claim 30, wherein the individual electrode terminals each have a cross-sectional area in the range from 0.0001 $mm^2$ to 1 $mm^2$.

32. An electrosurgical probe as in claim 26, further comprising a common electrode on the shaft, wherein the common electrode is disposed proximally of the electrode array and wherein the connector also provides for electrical coupling of the common electrode to the power supply.

33. An electrosurgical probe as in claim 26, further comprising a plurality of electrically isolated conductors disposed in the shaft and connecting the electrode terminals to the connector.

34. An electrosurgical probe as in claim 33 wherein the electrode terminals have an inherent capacitance, the probe further comprising a current limiting element connected across the power supply conductors to supplement the inherent capacitance of the electrodes.

35. An electrosurgical probe as in claim 34 wherein the capacitance of the electrodes and the current limiting element together form a series resonant output circuit.

36. An electrosurgical probe as in claim 34 wherein the current limiting element comprises a capacitor.

37. An electrosurgical probe as in claim 34 wherein the current limiting element comprises one or more inductors coupled in series between the conductors and the connector.

38. An electrosurgical probe as in claim 26, wherein the recessed surface is planar or convex.

39. An electrosurgical probe as in claim 26, wherein the shaft is cylindrical and the recessed surface is defined over a coaxial plane spaced radially inward from the cylindrical surface.

40. An electrosurgical probe as in claim 39, wherein the individual electrode terminals protrude over the released surface by a distance in the range from 0 mm to 2 mm.

41. An electrosurgical probe as in claim 26, wherein the electrode array has an area in the range from 1 $mm^2$ to 75 $mm^2$.

42. The probe of claim 26 wherein the electrode array includes at least three electrically isolated terminals having substantially the same potential.

43. The probe of claim 26 wherein the electrode array includes at least five electrically isolated terminals having substantially the same potential.

44. The probe of claim 26 further comprising a single common electrode disposed proximally from the electrode terminals, wherein voltage is applied between each of the electrode terminals and the single common electrode.

45. A method for treating prostate disease comprising:

engaging an electrode array including a plurality of electrically isolated terminals against prostatic tissue at a target site adjacent the urethra;

applying high frequency voltage between each electrode terminal in the electrode array and one or more common electrodes on or in the patient body; and independently controlling current flow through individual electrode terminals to inhibit power dissipation into the medium surrounding the target site.

* * * * *